US011311723B2

(12) United States Patent
Shah

(10) Patent No.: US 11,311,723 B2
(45) Date of Patent: Apr. 26, 2022

(54) MOTOR DEVICES FOR MOTOR NERVE ROOT STIMULATION

(71) Applicant: Jawad A. Shah, Flushing, MI (US)

(72) Inventor: Jawad A. Shah, Flushing, MI (US)

(*) Notice: Subject to any disclaimer, the term of this patent is extended or adjusted under 35 U.S.C. 154(b) by 0 days.

(21) Appl. No.: 17/367,659

(22) Filed: Jul. 6, 2021

(65) Prior Publication Data

US 2021/0322768 A1    Oct. 21, 2021

Related U.S. Application Data

(63) Continuation of application No. 16/751,631, filed on Jan. 24, 2020, which is a continuation of application No. 16/515,270, filed on Jul. 18, 2019, now Pat. No. 10,569,083, which is a continuation-in-part of application No. 13/293,964, filed on Nov. 10, 2011, now abandoned.

(60) Provisional application No. 61/412,484, filed on Nov. 11, 2010.

(51) Int. Cl.
*A61N 1/36* (2006.01)
*A61N 1/05* (2006.01)
*A61N 1/372* (2006.01)

(52) U.S. Cl.
CPC ....... *A61N 1/36003* (2013.01); *A61N 1/0556* (2013.01); *A61N 1/0558* (2013.01); *A61N 1/36062* (2017.08); *A61N 1/36157* (2013.01); *A61N 1/36178* (2013.01); *A61N 1/37247* (2013.01)

(58) Field of Classification Search
CPC ............ A61N 1/36003; A61N 1/36062; A61N 1/0556; A61N 1/0558; A61N 1/36157; A61N 1/36178; A61N 1/37247

USPC .......................................................... 607/48
See application file for complete search history.

(56) References Cited

U.S. PATENT DOCUMENTS

| 4,934,368 | A | * | 6/1990 | Lynch ................ A61N 1/36003 607/118 |
| 7,628,750 | B2 | | 12/2009 | Cohen et al. |
| 9,474,906 | B2 | | 10/2016 | Sachs et al. |
| 9,603,538 | B2 | | 3/2017 | Fisher et al. |
| 10,300,279 | B2 | | 5/2019 | Fraga Da Silva et al. |
| 2002/0161415 | A1 | * | 10/2002 | Cohen ................ A61N 1/36003 607/48 |
| 2005/0171579 | A1 | | 8/2005 | Taschen et al. |

(Continued)

FOREIGN PATENT DOCUMENTS

| CN | 106236377 A | 12/2016 |
| WO | 2018187241 | 10/2018 |
| WO | 2019032890 | 2/2019 |

*Primary Examiner* — Erin M Piateski
(74) *Attorney, Agent, or Firm* — Kohn & Associates, PLLC

(57) ABSTRACT

A motor device for stimulating muscle, including at least one electrode for generating electric current operatively attached to an electrode array and exposed on an inner surface of an array body, and a programming mechanism of a computer that executes an algorithm stored on non-transitory computer readable medium and includes an information storage mechanism and a user-operated interface in electrical connection with said at least one electrode for programming operation of said at least one electrode, said motor device being implanted in an individual and applying electric current to nerves at an area above an area of neurological damage.

16 Claims, 11 Drawing Sheets

(56) References Cited

U.S. PATENT DOCUMENTS

| | | | |
|---|---|---|---|
| 2008/0140169 A1* | 6/2008 | Imran | A61N 1/0551 607/117 |
| 2008/0177339 A1* | 7/2008 | Bolea | A61N 1/05 607/3 |
| 2009/0118780 A1* | 5/2009 | DiLorenzo | A61N 1/36114 607/2 |
| 2016/0106994 A1* | 4/2016 | Crosby | A61N 1/36135 600/13 |
| 2016/0128620 A1 | 5/2016 | Iriki et al. | |
| 2017/0120057 A1 | 5/2017 | Hoffer et al. | |
| 2017/0246450 A1 | 8/2017 | Liu et al. | |
| 2018/0056066 A1 | 3/2018 | Boggs et al. | |
| 2018/0178008 A1 | 6/2018 | Bouton et al. | |
| 2019/0021883 A1 | 1/2019 | Herr et al. | |
| 2019/0191524 A1 | 6/2019 | Graf et al. | |

* cited by examiner

MOTOR DEVICES FOR MOTOR NERVE ROOT STIMULATION

BACKGROUND OF THE INVENTION

1. Technical Field

The present invention relates to electrical stimulation of nerves. In particular, the present invention relates to electrical stimulation of nerves to move muscles and regain function of the body after neurological damage.

2. Background Art

Circumstances arising from trauma, such as motor vehicle accidents, falls, etc., can result in neurological damage involving the spinal cord such that the individual becomes paralyzed or loses feeling in one or many parts of the body. In addition, there are a variety of diseases that involve the spinal cord, and can cause progressive loss of muscular control, severely reducing the normal function and quality of life of the individual. Likewise, there are a variety of conditions that can cause an individual to feel pain, whether chronically or episodically, in various parts of the body. These and other causes and conditions present significant challenges to individuals and their families who strive to help the afflicted person cope with such disabilities.

The spinal cord extends from the base of the brain to about the waist, extending to the space between the first and second lumbar vertebrae, and is protected by bony processes in the vertebral column. The eight vertebrae in the neck are called cervical vertebrae, and the one at the top is labeled C-1. Following the cervical vertebrae are the twelve thoracic, five lumbar, and five sacral vertebrae.

The spinal cord nerves, known as the upper motor neurons, function to carry electrical impulses to and from the brain to spinal nerves along the spinal tract. Lower motor neurons are the spinal nerves that branch out from the spinal cord and communicate with specific regions in the body, initiating actions such as muscle movement. The lower motor neurons emanate from specific vertebrae such that injury to the spinal cord at a particular vertebra causes specific dysfunction in the afflicted person. In general, injuries higher up in the vertebral column will cause higher levels of dysfunction. The central problem with neurological damage in the spinal column is the loss of communication along nerves at various levels of the spinal column.

There are several methods that are currently used to treat spinal column damage. Surgery, a variety of drugs, and physical therapy are currently used. Experimental treatments include use of stem cell, autologous transplants, and genetically engineered biological agents.

For example, methylprednisolone is often given within eight hours of injury, and while not a cure, it has shown to provide mild improvement through reducing damage to nerve cells and decreasing inflammation; however, this treatment has fallen out of favor due to complications. Surgery can be used to repair disks or vertebrae that are compressing the spine. Physical therapy is used to help persons relearn how to move muscles or strengthen other muscles needed to perform tasks that were previously done with other muscles.

None of these treatments has a high success rate with paraplegics. Surgery has attendant risks, and frequently results in fibrosis at the surgical site. The use of drugs may not effectively target specific tissues, because drugs must pass through general circulation to get to the afflicted site, and there may be many adverse effects, such as liver damage and other unintended consequences of treatment. Physical therapy seems to provide mostly palliative results, due to increased blood flow in exercising of limbs, and cannot provide neurological stimulation at specific sites when it is needed. Experimental treatments may only be available in clinical studies, only in specified institutions or locations, and so on, and they often have not been fully tested for safety and efficacy. Complete spinal disruption, anatomical or physiological, has no current treatment for the complete return of function.

Spinal cord stimulators have been used to reduce chronic pain by implantation of wires near the spinal cord. The reduction rate can be 50% or greater. Chronic pain is reduced by interrupting nerve conduction of the pain with low level electrical stimulation produced by a spinal cord stimulator. In essence, the spinal cord stimulator produces an electrical current that competes for the brain's attention with the pain, such that the brain focuses on the electrical current and not the pain.

U.S. Pat. No. 7,610,096 to McDonald, III, discloses methods for the treatment of CNS damage, and includes inducing in a subject in need of such treatment, a therapeutically effective amount of functional electrical stimulation (FES) sufficient to evoke patterned movement in the subject's muscles, the control of which has been affected by the CNS damage. The induction of FES-evoked patterned movement at least partially restores lost motor and sensory function, and stimulates regeneration of neural progenitor cells in the subject person. The treatment is thought to work by inducing FES-evoked patterned body movements that regenerate neural cells such that CNS damage previously thought beyond repair is repaired, and function previously thought permanently lost is at least partially restored. Without being bound to a particular theory, the FES-evoked patterned movements are thought to stimulate neural regeneration by stimulating neural activity in a central pattern generator. Physiologic and metabolic demands placed on cells comprising the spinal circuit may activate cellular processes that promote new neural cell birth and survival. FES can thereby harness the innate plasticity of the nervous system. While recovery of function is possible to the extent that neurons can be created, this particular method does not provide a way to recover function when the repair or regeneration needed is too great or not possible.

U.S. Pat. No. 7,778,704 to Rezai discloses a method of affecting physiological disorders by stimulating a specific location along the sympathetic nerve chain. A method is disclosed of affecting a variety of physiological disorders or pathological conditions by placing an electrode adjacent to or in communication with at least one ganglion along the sympathetic nerve chain and stimulating the at least one ganglion until the physiological disorder or pathological condition has been affected. Physiological disorders that may be treated include, but are not limited to, hyperhydrosis, complex regional pain syndrome and other pain syndromes such as headaches, cluster headaches, abnormal cardiac sympathetic output, cardiac contractility, excessive blushing condition, hypertension, renal disease, heart failure, angina, hypertension, and intestinal motility disorders, dry eye or mouth disorders, sexual dysfunction, asthma, liver disorders, pancreas disorders, and heart disorders, pulmonary disorders, gastrointestinal disorders, and biliary disorders.

Harkema, et al. (The Lancet, May 20, 2011) describe a method of nerve stimulation by implanting an epidural spinal cord stimulation unit. Upon stimulation, patients were able to stand with balance assistance and eventually voluntarily achieve toe extension, ankle deflection, and leg flexion. The method of Harkema employs an electrode body having slight curvature, which is placed on the dura. The shape and the placement of the electrode body thereby allow a relatively coarse degree of focusing of the electrical current. The device and method of Harkema does not allow for fine control over the location, intensity, phase, and other characteristics of the electrical fields that are applied to the nerve root. In addition, the selected patients did in fact not have complete injuries in that the sensory part of the cord remained functional. This implies that partial retention of function must have existed and was exploited to help return function.

Thus, there remains a need for finer control of electrical stimulation.

While these methods have been developed that electrically stimulate the central nervous system or spinal cord, full recovery of movement has not yet been possible. Furthermore, damage to muscles can actually occur with FES when a muscle is contracted by electrical stimulation but opposing muscles are not relaxed as during normal function of a limb, resulting in tears, blisters, or burns. Other problems persons have experienced include dizziness, and autonomic dysreflexia, which is an over-activity of the autonomic nervous system causing an abrupt onset of excessively high blood pressure. Persons can experience discomfort during treatment, such as "pins and needles" under their skin, and a tingling sensation caused by the flow of electrical currents passing through their body. These sensations can be overcome, but the device must be tuned to the user's comfort level (i.e., current type, modulation, waveform, pulse duration and repetition rate, and intensity) or treatment can be unsuccessful. On occasion, the FES electrode's adhesive or gel can cause users to develop skin irritation and rashes. FES treatment is also not recommended for several person groups whose conditions would be sensitive to electrodes.

The spinal cord itself carries central nervous motor information element within larger bundles of flowing neurons. Precise targeting is difficult. Distal nerves are too numerous and difficult to access for simulation purposes as well, although selective stimulation may extend function in conjunction with the current device. Nerve roots on the other hand are well organized into discrete bundles that are more conducive to exploit for functional purposes, and provide very easy access. To date, no formal attempt to stimulate the motor nerve roots, as opposed to the spinal cord or a distal peripheral nerve, in complete paraplegic or quadriplegic patients has caused return of function and muscle bulk achieving functional results. Stimulation of motor nerve roots has not been exploited to achieve full functional movements.

Therefore, there remains a need for a treatment that addresses neurological damage to the spinal column without adverse affects and that allows a person to regain mobility and a sense of independence, and/or reduce or eliminate various sources of pain.

SUMMARY OF THE INVENTION

The present invention provides for a motor device for stimulating muscle including at least one electrode for generating electric current operatively attached to an electrode array and exposed on an inner surface of an array body, and a programming mechanism of a computer that executes an algorithm stored on non-transitory computer readable medium and includes an information storage mechanism and a user-operated interface in electrical connection with the at least one electrode for programming operation of the at least one electrode, the motor device being implanted in an individual and applying electric current to nerves at an area above an area of neurological damage.

DESCRIPTION OF THE DRAWINGS

Other advantages of the present invention are readily appreciated as the same becomes better understood by reference to the following detailed description when considered in connection with the accompanying drawings wherein.

DETAILED DESCRIPTION OF THE INVENTION

Figure 1:
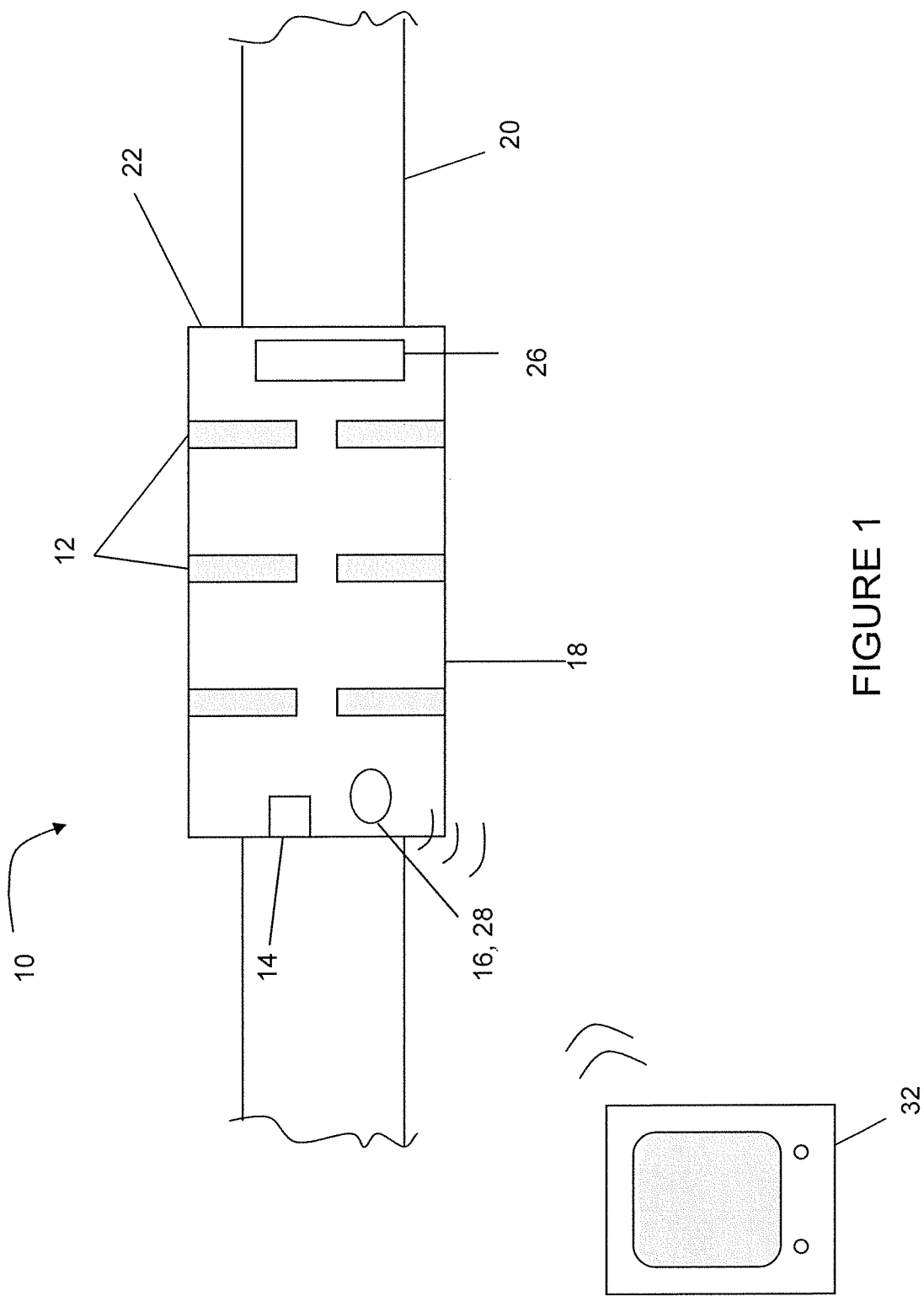
FIG. 1 is a top view of the motor device.

The present invention provides methods of stimulating muscle through electric current that is especially useful in treating paraplegics, hemiplegics, and quadraplegics, as well as other kinds of neurological damage. The present invention also provides a motor device, shown generally at 10 in FIG. 1, for bypassing or bridging an area of neurological damage and providing muscle stimulation that is used to perform the above method, including at least one electrode 12 having a mechanism 14 for generating electric current, and a programming mechanism 16 for programming the at least one electrode 12. The method and device 10 of the present invention are used to allow an individual with neurological damage to regain use of their muscles and limbs that have been rendered non-functional due to their neurological damage, as well as generally stimulating muscle in a variety of uses.

The terms "bypass" or "bypassing" as used herein, refer to circumvention of diseased areas of the body, preferably non-functioning neural circuits. Alternatively, this concept can also be referred to as a "bridge" or "bridging" non-functioning neural circuits in the body in order to access functioning neural circuits. These terms can be used interchangeably herein without departing from the spirit of the invention.

The term "neurological damage" refers to any damage relating to nerves or the nervous system. "Neurological damage" can include specifically neural damage wherein neurons are no longer able to communicate and send signals to other neurons in a neural circuit.

Figure 2:
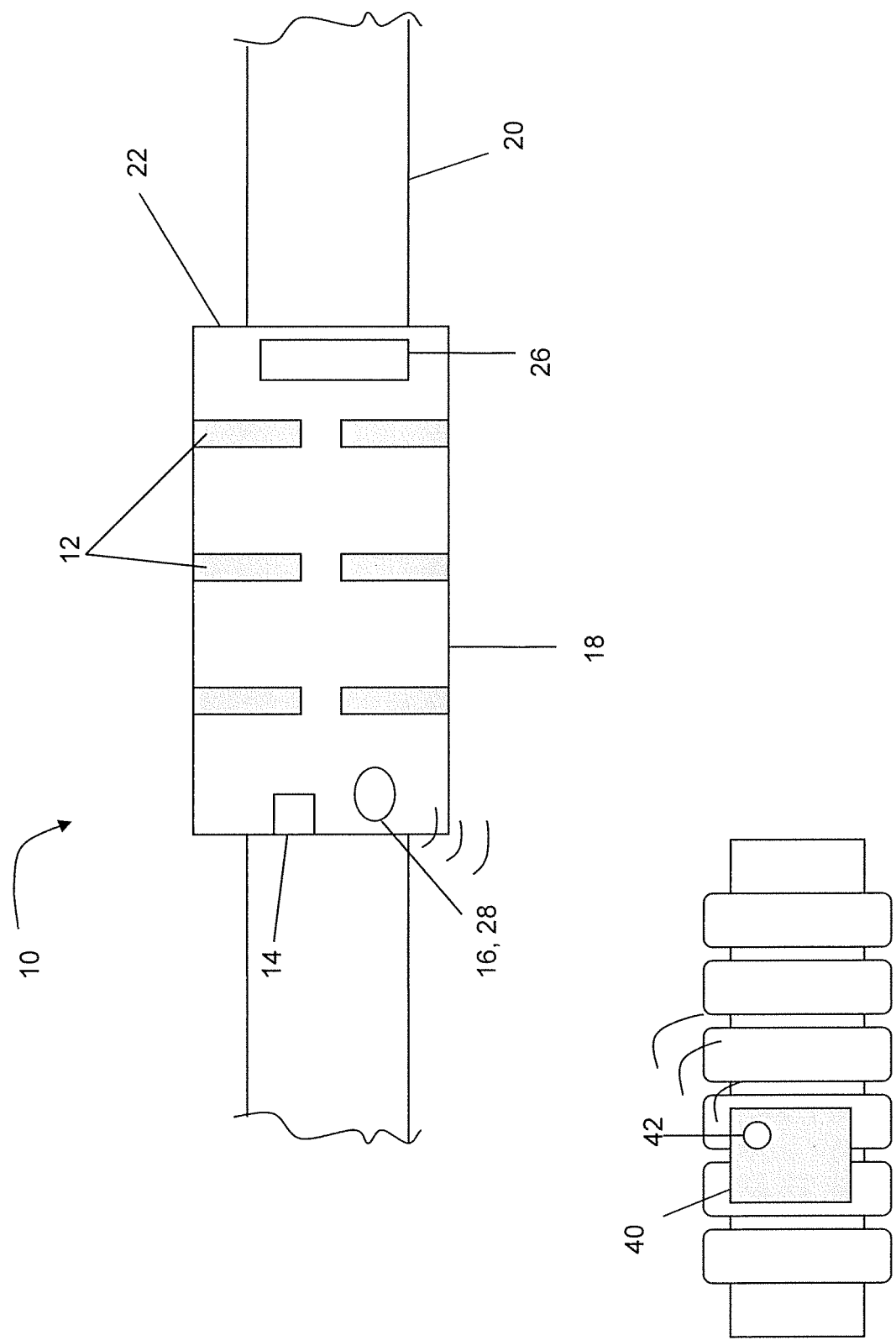
FIG. 2 is a view of the motor device in communication with the sensory device.
Figure 3:
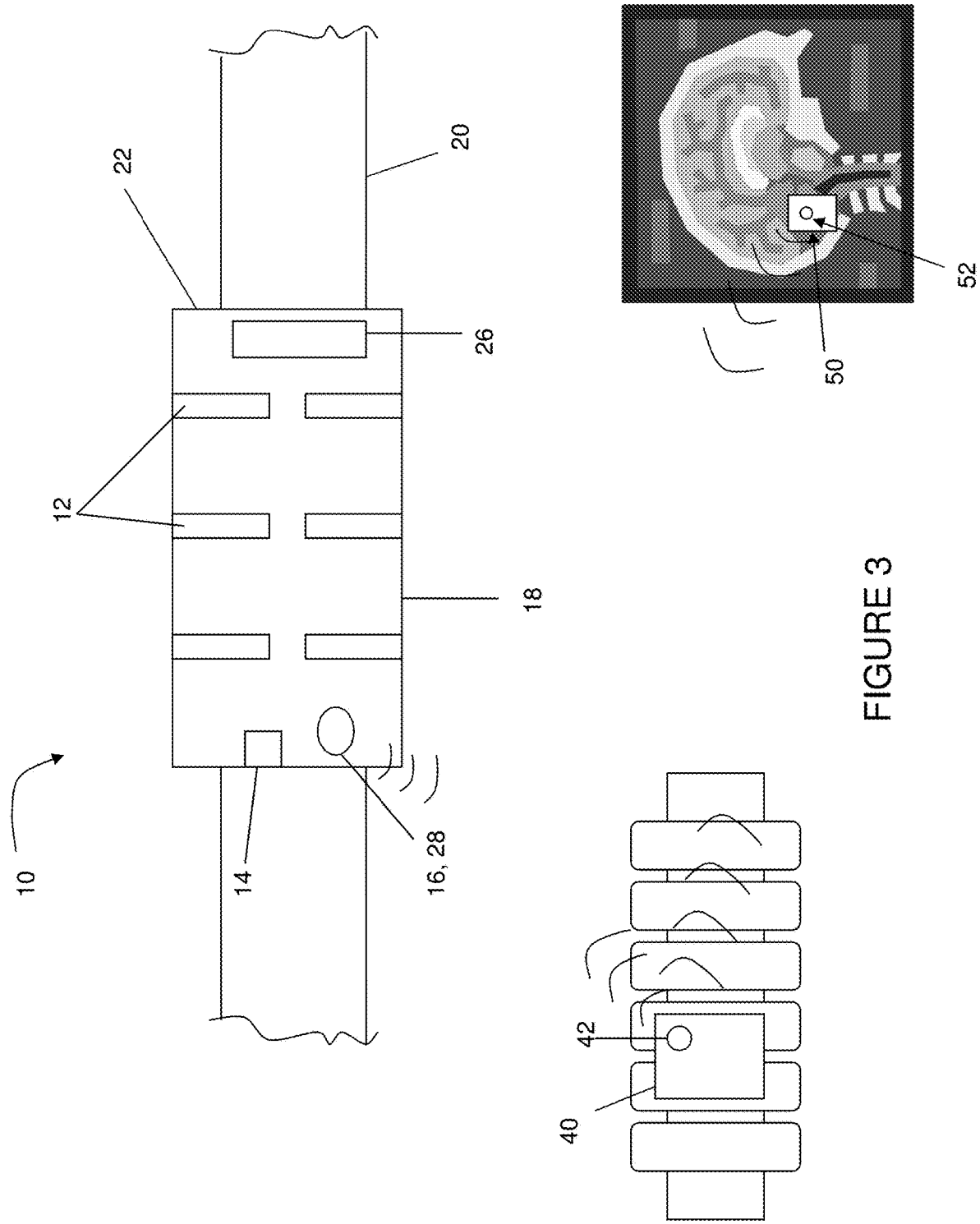
FIG. 3 is a view of the motor device in communication with the sensory device and the information harvesting device.
Figure 4:
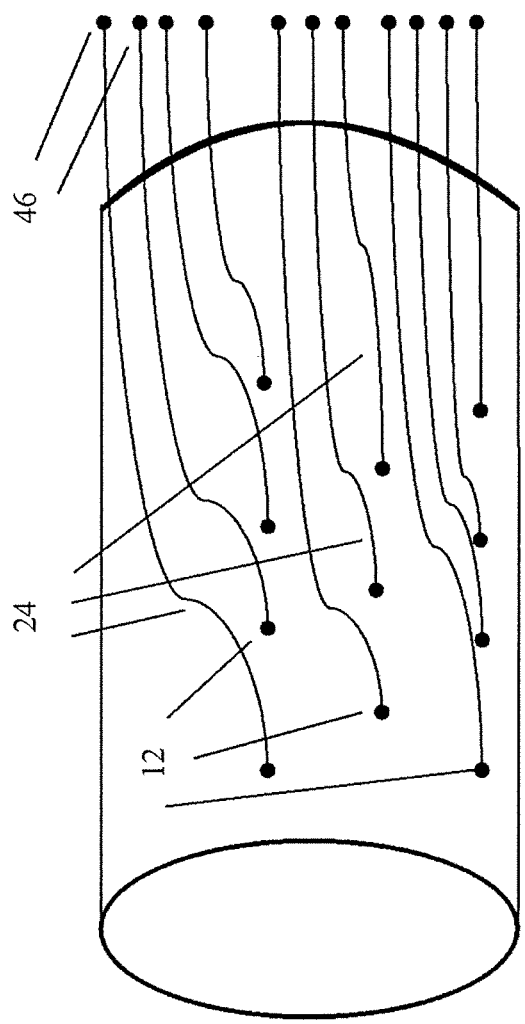
FIG. 4 is a view of the motor device that shows one of the available patterns of wire leads and electrode contacts.
Figure 5:
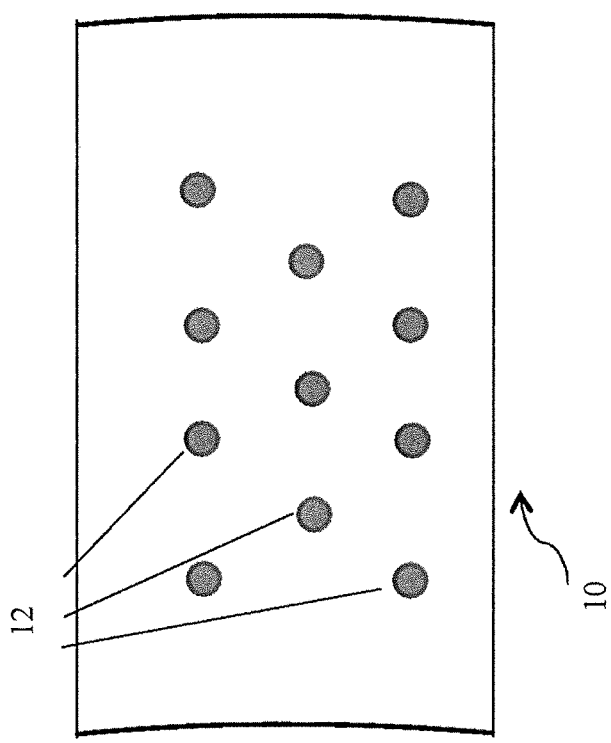
FIG. 5 is a view if the interior of the motor device, showing multiple electrode contacts.

Most generally, the present invention provides for a motor device 10 for stimulation of muscle including at least one electrode 12 for generating electric current operatively attached to an electrode array 18 and exposed on an inner surface 34 of an array body 19, and a programming mechanism 16 of a computer 28 that executes an algorithm stored on non-transitory computer readable medium and includes an information storage mechanism 30 and a user-operated interface 32 in electrical connection with the at least one electrode 12 for programming operation of the at least one electrode 12, the motor device 10 being implanted in an individual and applying electric current to nerves at an area above an area of neurological damage As shown in FIGS. 2 and 3, the motor device 10 can be in the form of a specially designed electrode array 18 that can be deployed and wrapped around a nerve 20 (preferably the nerve root). The electrode array 18 can be considered as a cuff 22 that hugs the nerve root 20 or a lead that lies or is placed parallel to the nerve root 20 or that can lie or be placed in the epidural space that make contacts 46 with the area requiring electrical stimulation, as shown in FIG. 4. The electrode array 18 can also be positioned in or around any other suitable place for nerve stimulation.

The electrode array 18 can contain operatively attached thereto multiple electrodes 12 for independent programming of electrical output along an array body 19, shown for example in FIG. 5, and FIGS. 8A-8E. The electrodes 12 appear as a multiplicity of dots or discs exposed on one side (the inner surface 34) of the array body 19, and they are the contact areas that conduct electrical impulses to the surface of the nerve root. The amount of electrodes 12 used can vary, however, and as many electrodes 12 as possible can be used in the available space in the electrode array 18 in order to stimulate the nerve root 20. The electrodes 12 can be aligned about the radius of the array body 19, as in FIG. 8A, or alternating about the radius, as in FIG. 8B.

The side of the array body 19 wherein the contacts are exposed are placed in proximity to the nerve root and can be referred to as its proximal or inner surface 34. Each dot or disc contact of the electrode 12 includes a wire lead 24 that passes through the array body 19 from the inner surface 34 and exits at the distal or outer surface 36 of the array body 19. The leads 24 have a contacting face (not shown) that is flush with or very slightly inset from the inner surface 34 of the electrode array 18. After exiting the array body 19, the leads 24 are covered with an insulating polymer, such that the leads 24 cannot directly contact one another. The insulating polymer materials can be the same or different than the materials of the array body 19 described below. Appropriate insulating material for the leads 24 can include, but are not limited to, silicones (including polydimethylsiloxane (PDMS, Dow Corning Sylgard 184)), photo-patternable silicone (Dow Corning WL5150), hydroxylated urethane, polyimides, TEFLON® (polytetrafluoroethylene, DuPont), or other flexible polymers having a high dielectric constant. All materials of the leads 24 are medical grade and/or FDA approved for implantation. The leads 24 are of a sufficient length to permit their connection to a source of electrical current.

Figure 8A:
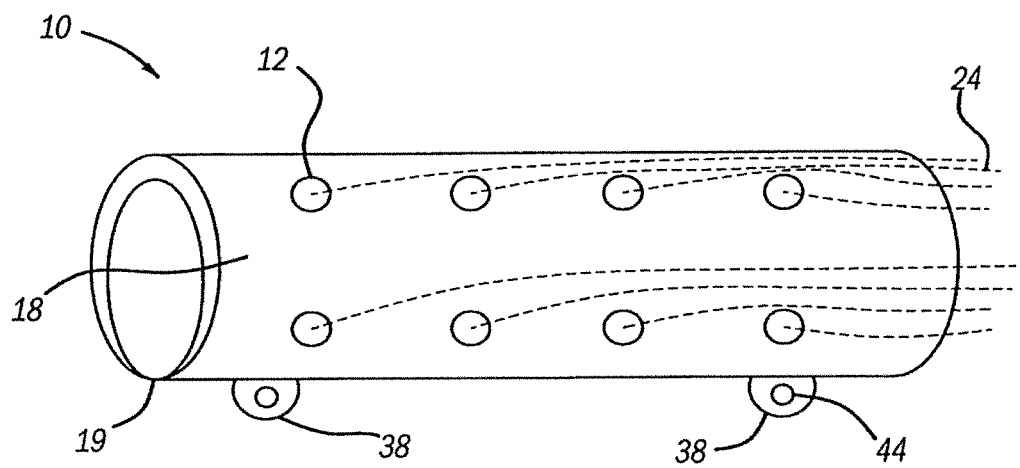
FIG. 8A is a side perspective view of the motor device.
Figure 8B:
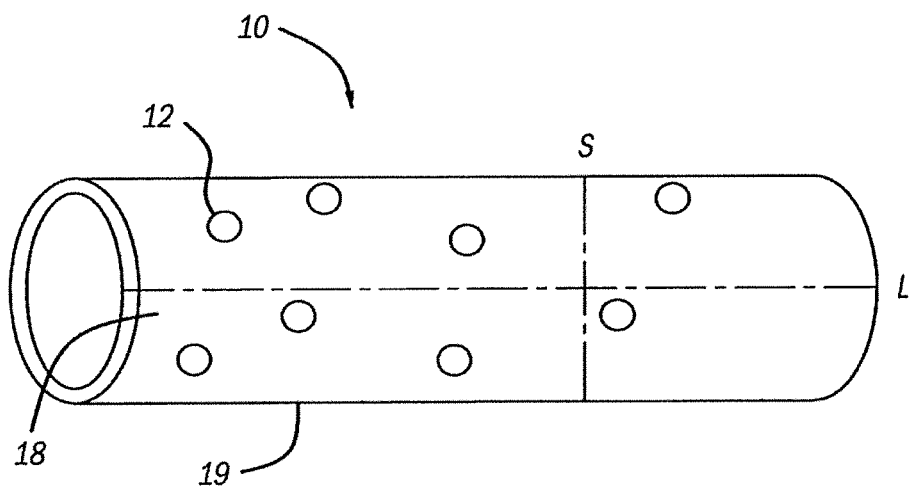
FIG. 8B is a side perspective view of the motor device.

The array body 19 can have a long axis L from 2 to 3 cm, shown in FIG. 8B. When mounted on a nerve root, this axis will be oriented along the length of the nerve. The array body 19 also can have a short axis S from 2.2 to 2.8 cm. This short axis can be wrapped around the nerve root, whose natural diameter is approximately 4-5 mm.

The disc or dot contacts of electrodes 12, along with their leads 24, can be composed of any variety of materials that include, but are not limited to, surgical stainless steel, gold wire, an indium/gold alloy, photo-patterned gold, layers of photo-patterned chromium and gold, or another conductor that is selected for the properties of low impedance, chemical stability and low bioreactivity, as suitable for a chronically implanted medical device. The conductor material must be suitable and stable enough to allow for chronic implantation for periods of months to years. The contacts of the electrodes 12 are arranged along the inner face 34 of the array body 19 in circumferential rows that run across the short axis of the array body 19, with leads 24 running toward the outer surface 36. The appearance of the array 18 on the inner proximal face 34 of the array body 19 is of lines of dots, 0.1 to 2.5 mm diameter, extending across the short face of the array body 19. The distance between lines may be varied, from 1 mm to 1 cm, depending on the specific performance requirements of the intact array 18.

The array body 19 can be formed as a flat sheet and composed of a biologically non-reactive polymer that is pliable and is able to easily wrap around the nerve root 20 to conform to its shape, such as, but not limited to, silicones (including polydimethylsiloxane (PDMS, Dow Corning Sylgard 184)), photo-patternable silicone (Dow Corning WL5150), hydroxylated urethane, polyimides such as Pyralin 2611, TEFLON® (DuPont), polyrurethane, polydimethylsiloxane or other silicones, or other polymers. The array body 19 materials should have the following properties: it is an electrical inert polymer, the polymer is chemically inert and has low bio-reactivity, the polymer is FDA approved for implantation, and the polymer is very soft with a low Young's modulus to minimize nerve damage.

The diameter of the electrode array 18 can vary depending on the size of the nerve root that it is surrounding. TABLES 1-4 provides examples of diameters of nerve roots and electrodes. TABLE 4 shows the relationship between contact diameter and number of contacts based on gross electrode dimensions.

TABLE 1

| | from Guvencer 2007. J Clin Neurosci 15: 192-7. | | Width, mm | |
|---|---|---|---|---|
| level | mean dia, mm | sd | mean | sd |
| L1 | 4.9 | 0.5 | 15.4 | 1.6 |
| L2 | 5.5 | 0.6 | 17.3 | 1.9 |
| L3 | 6.5 | 0.7 | 20.4 | 2.2 |
| L4 | 7.2 | 0.9 | 22.6 | 2.8 |
| L5 | 7.5 | 1 | 23.6 | 3.1 |

TABLE 2

| | from Ebraheim 1997, Clin Orthoped 340,230-5 | | | Width range | | Width |
|---|---|---|---|---|---|---|
| level | range, mm | ave, mm | sd | max = | min = | ave |
| L1 | 4-6 | 4.9 | 0.7 | 12.6 | 18.8 | 15.4 |
| L2 | 4-7 | 5.5 | 0.9 | 12.6 | 22.0 | 17.3 |
| L3 | 5-8 | 6.3 | 1 | 15.7 | 25.1 | 19.8 |
| L4 | 6-8 | 7.0 | 0.9 | 18.8 | 25.1 | 22.0 |
| L5 | 5-8 | 7.0 | 0.9 | 15.7 | 25.1 | 22.0 |

TABLE 3

Diameter est from Hogan (1996) areas

| level | Hogan's area | fold difference | Ebraheim diameter |
|---|---|---|---|
| T12 | 0.7 | 1 | |
| L1 | 0.73 | 1.042857143 | 4.9 |
| L2 | 1.3 | 1.857142857 | 5.5 |
| L3 | 2.4 | 3.428571429 | 6.3 |
| L4 | 1.87 | 2.671428571 | 7 |
| L5 | 2.31 | 3.3 | |
| S1 | 2.62 | 3.742857143 | |
| S2 | 1.18 | 1.685714286 | |

TABLE 4

| Nerve root (1) | Width (circum.) of electrode body, mm | Center-to-center contact distance in mm per number of circumferential contacts | | | | | Width range | |
|---|---|---|---|---|---|---|---|---|
| | | 4 | 6 | 8 | 12 | 16 | max = 110% | min = 90% |
| Diameter, mm | = 3.1416 × dia | | | | | | | |
| 4 | 12.6 | 3.14 | 2.09 | 1.57 | 1.05 | 0.79 | 13.8 | 11.3 |
| 4.5 | 14.1 | 3.53 | 2.36 | 1.77 | 1.18 | 0.88 | 15.6 | 12.7 |
| 5 | 15.7 | 3.93 | 2.62 | 1.96 | 1.31 | 0.98 | 17.3 | 14.1 |
| 5.5 | 17.3 | 4.32 | 2.88 | 2.16 | 1.44 | 1.08 | 19.0 | 15.6 |
| 6 | 18.8 | 4.71 | 3.14 | 2.36 | 1.57 | 1.18 | 20.7 | 17.0 |
| 6.5 | 20.4 | 5.11 | 3.40 | 2.55 | 1.70 | 1.28 | 22.5 | 18.4 |
| 7 | 22.0 | 5.50 | 3.67 | 2.75 | 1.83 | 1.37 | 24.2 | 19.8 |
| 7.5 | 23.6 | 5.89 | 3.93 | 2.95 | 1.96 | 1.47 | 25.9 | 21.2 |
| 8 | 25.1 | 6.28 | 4.19 | 3.14 | 2.09 | 1.57 | 27.6 | 22.6 |
| 8.5 | 26.7 | 6.68 | 4.45 | 3.34 | 2.23 | 1.67 | 29.4 | 24.0 |

Figure 8C:
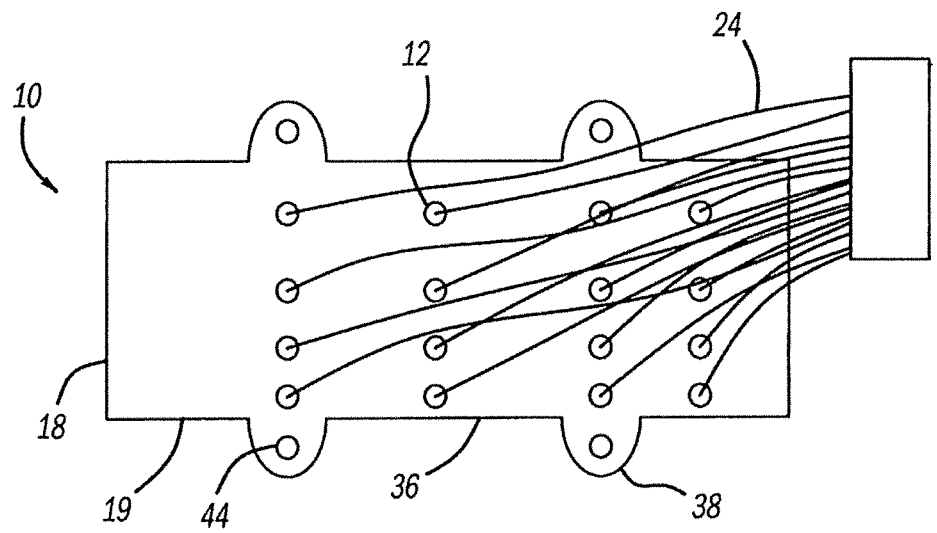
FIG. 8C is a view of an outer surface of flattened array body with leads.
Figure 8D:
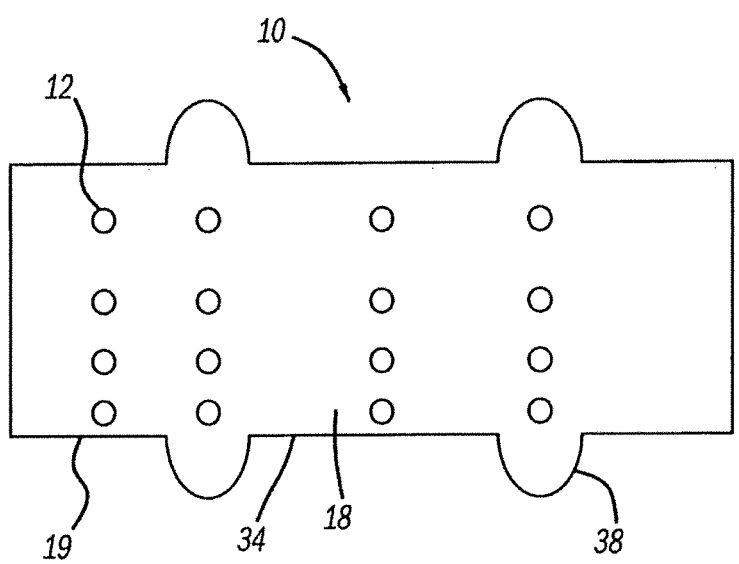
FIG. 8D is a view of an inner surface of flattened array body.
Figure 8E:
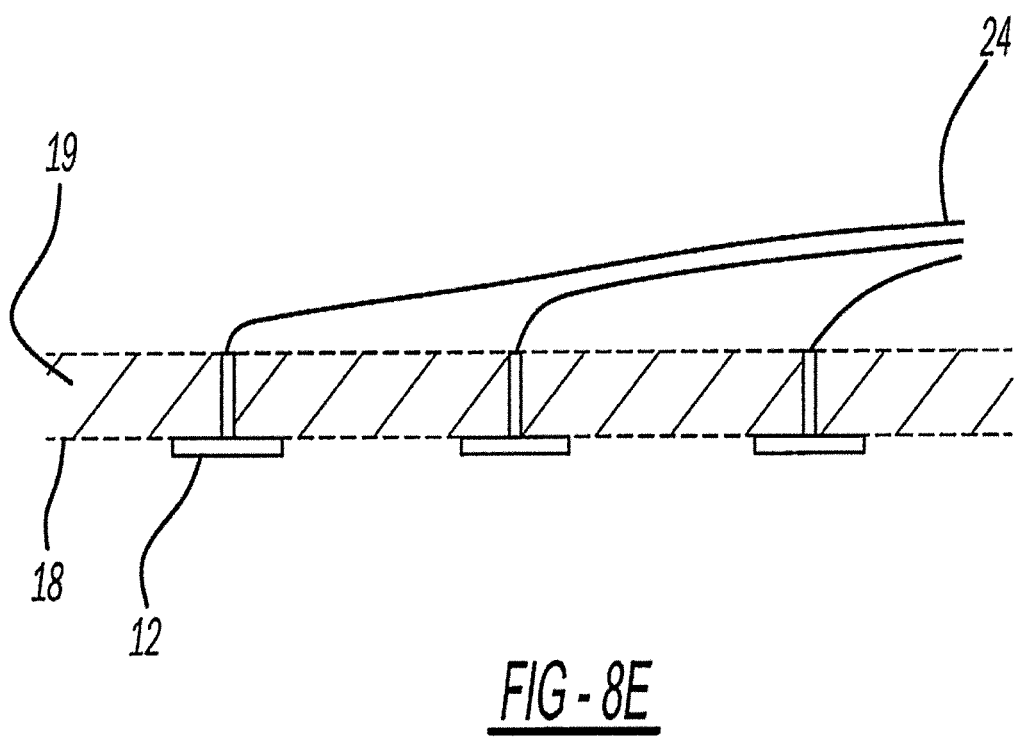
FIG. 8E is a cross-sectional view of the motor device.

The electrode array 18 can be secured into place by tissue glue, sutures, stay screws, or alternatively, the stiffness of the device 10 with specially designed silicon holders with imbedded electrodes 12. Electrode array 18 can be produced with multiple flaps or flange 38 along the long axis. For example, four flaps 38 are shown in FIGS. 8C and 8D. These flaps 38 can be supplied with small holes 44, to accommodate suturing by the surgeon. The flaps 38 can be arranged in opposition or can alternate, thereby allowing options for the surgeon. The suturing is performed such that the body 19 of the electrode array 18 makes direct contact with the nerve root, but also such that it does not impose compression upon the nerve root. With time, scar tissue helps prevent migration of the electrode array 18. By securing the electrode array 18 in a position symmetrical around the nerve root 20, the applied electrical current can be exploited at any particular electrode 12, or combination of electrodes 12, thereby stimulating a more diverse cross-section of nerve roots 20. The electrodes 12 can play off one another in terms of the cathodes and the anodes, as required to avoid tissue damage, and can apply steering current using tripodal electrodes or other arrangements of electrodes, but this allows maximal control in the stimulation of the nerve roots 20 and particularly of nerve fascicles within nerve roots. The principle of motor nerve activation can also be extended to the use of multiple electrode arrays 18, placed on nerves or nerve roots 20 selected for their ability to stimulate muscular contraction. Such multiple electrode arrays may be stimulated in a coordinated fashion, as required, to obtain the desired capabilities that result from muscular contraction, such as locomotion and resolution of foot drop and of arm paresis.

The electrodes 12/electrode array 18 can be constructed in whole or in part by 3D printing technology. Such 3D printing technology preferably has two components 1) a mapping step, using fiber optic cameras to guide the surgeon and to measure nerve dimensions; and 2) a constructing step, using a 3D printer that is fitted with printer heads or other mechanisms to deposit or print in 3D space using technology concepts of additive manufacturing.

For example, for the mapping step in the case of motor nerve roots, once the surgeon has accessed the motor nerve roots, endoscopes can be used to chart the contours and various dimensions of the nerve root surface. Small incisions can provide access of the endoscopes. Data collected via optical fibers or other methods of transmission can be decoded by software to the actual dimensions of the nerve roots, as well as other local features of significance.

The constructing step can be accomplished in two different ways with a constructing device including 3D printing. First, the constructing step can be extracorporeal, or outside the body. Second, the constructing step can be intracorporeal, or within the body. Both technologies use principles and means employed in additive manufacturing, or 3D printing. Thus, they both can be controlled by software that can translate the mapping data from the initial mapping step, thereby controlling the deposition of material.

The extracorporeal construction can produce electrodes 12 within the surgical field, using principles of 3D printing, and whose electrodes 12 can subsequently be placed around or adjacent to the nerves of interest. Alternatively, electrodes 12 can be produced at remote locations and surgically implanted at a later time.

The intracorporeal construction can utilize the same principles, with the exception that the printing events occur within the body. To accomplish the latter, print heads can be controlled by means of the endoscopes that are used to map the nerve surface. In an ultimate form of the intracorporeal device, mapping and printing devices can be joined into a single device whose functions are coordinated such that electrode construction can be accomplished immediately after mapping of the nerve surface.

Both methods of construction can construct nerve electrodes 12 having at least two distinctly different electrical properties, i.e, those of the insulator and of the conductor. The substrate that provides such properties is different materially and chemically; thus, the constructive device includes at least two different print heads or other means of deposition. One such print head can supply the insulating material that forms the electrode 12 body. Such material can be a soft elastomeric plastic or other nonconducting polymer that conforms to the outer surface of the nerve. This insulating material provides a soft, compliant surface, so to conform to the shape of the nerve root or nerve of interest. Such material can have the desired conformation and flexibility upon construction, or can be photo-curable, utilizing an optical fiber directing ultraviolet light. The other print head can supply the electrically conducting material. Such material, which comes to direct or very close contact with the nerve root, can also be a flexible and compliant material. Examples of such materials are alloys of indium and gallium, whose admixture can be used to produce electrical conductors that are soft, conforming and stretchable. Such indium/gallium alloys are liquid at room temperature, yet form a "skin" upon contact with air or other weak oxidant. Thus, such a printer can be fitted with print heads that provide the conductor, and that provide a weak oxidant in sterile saline.

Therefore, the present invention provides for a method of preparing electrodes, by mapping nerve dimensions and features, and constructing electrodes with a 3D printer either extracorporeally or intracorporeally.

The electrode array 18 can further include at least one generator or battery 26 that provides electrical current to leads 24 that causes electrical transmission through nerves distal to the point of contact. Preferably, the battery 26 has a long life so that it does not need to be replaced often or require additional surgery. Preferably, the battery 26 includes enough inputs to connect with and to handle various energy output requirements by all of the components of the device 10.

As mentioned above, the electrode array 18 can be programmable and thus includes a programming mechanism 16 such as a computer 28 to execute an algorithm or software stored on non-transitory computer readable medium and a storage mechanism 30 to store the algorithm or software and any data collected or produced by the algorithm or software, such as RAM, ROM, flash storage, cloud-based storage, or any other storage mechanisms. Preferably, the computer 28 includes a user-operated interface 32 that can be programmed or operated by a user, such as a doctor or the person. The computer 28 via the algorithm directly sends signals to the device 10 to cause fluid and natural motion, such as moving a limb or walking. The computer 28 can also communicate wirelessly with a remote interface 32 (shown in FIG. 1), such as, but not limited to, a smart phone, or a touch screen device, a voice-activated device, or a thought-activated device operated directly by the person's own brain signals.

The algorithm can include instructions such as, but not limited to, how often to apply electric current, which nerve to apply current to, and how strong is the applied current. Additional parameters can be programmed and set and can include any combination of the following: the timing of electrical potential applied at different electrodes 12 in the electrode array 18 and/or in multiple electrode arrays used on a multiplicity of nerves and/or nerve roots 20; varying the intensity of electrical current applied at different electrodes 12 in the electrode array 18; the use of variable frequency trains; relaxation kinetics; stimulation frequency; shortening history; and random modulation of parameters, including: constant stimulation, randomized frequency, randomized current amplitude, and randomized pulse width. The battery 26, leads 24, electrodes 12, and program parameters are all adjusted to minimize pain felt by the person.

Most generally, a method of stimulating muscle in a person having neurological damage is provided by applying electric current to nerves, bypassing or bridging an area of neurological damage, and moving the muscle in a natural manner. Preferably, this method is performed with the motor device 10 as described above. While the method can be used with any type of muscle damage, most preferably, the present invention takes advantage of the organization of motor nerves inferior to the spinal level transected by injury or affected by disease. In other words, the muscles can be stimulated to move as if the individual has not experienced any neurological damage and natural flowing movement (i.e. not jerky movement) of the muscles can be produced.

The electric current can be applied to various nerves, including, but not limited to, central nerves, nerve roots, or peripheral nerves. Nerve roots carry very specific information to well mapped out myotomes and therefore this information can be exploited in this mapping to stimulate the muscle groups required to cause motion. Preferably, electric current is applied to a nerve bundle in order to stimulate a muscle group instead of just a single muscle, in order to provide natural movement. In other words, the stimulation is a coordinated muscle group stimulation. Electric current can be applied by inserting the motor device 10 including electrodes 12 into the spinal canal, or selected peripheral nerves, so that they become in intimate contact with nerve roots therein. Alternatively, the device 10 including electrodes 12 can be placed in close proximity of specific sensory (afferent) neurons. As described above, the electrode array 18 of the device 10 can be wrapped around the nerve root 20 or lie parallel to the nerve root 20. In addition, more specifically, the electrode array 18 can be placed along the nerve root at the L5-S1 level, parallel to the S1 nerve root. Stimulation of the nerves can generally be within levels T12 through S1. Stimulation can also be to any individual axon within a nerve root. The use of a multiplicity of contacts of electrodes 12 within a nerve root can allow for selective stimulation of individual axons, stimulation of combinations of axons, summation by multiple contacts along individual axons, variations of frequency and intensity, and other individual and combined stimulatory events, such that muscular contraction is caused as desired.

More specifically, the motor device can be inserted by a method such as, but not limited to, translaminar percutaneous insertion, translaminar insertion via surgical laminotomy, surgical foraminotomy, and surgical implantation around and adjacent to a peripheral nerve. In each insertion technique, nerves, central nerves, nerve roots, or peripheral nerves can be accessed. The device 10 can be deployed percutaneously or with direct surgical visualization for any technique. The extraforaminal route places the device 10 directly over the nerve root. The translaminar route places the device 10 around the nerve roots and parallel to the nerve root. With an intradural route, the dura is opened and the device 10 is placed directly over a nerve root, resulting in a very sensitive placement and robust stimulation. Epidural stimulation adjacent to the nerve root can also stimulate the nerve root to increase effectiveness to increase or decrease muscle tone, and epidural placement in the thoracic spine or cervical spine area can be used to stimulate the spinal cord and the variety of movements can be specifically programmed. The use of multiple devices 10 moreover can be used for coordinated stimulation of major muscle groups used for walking and other activities. The device 10 can be attached to a sensory device 40 (i.e. sensory electrodes, described below) to send signals above the spinal cord injured level.

As a result of the electric potential provided by the electrodes 12, nerve signals can cross the neuromuscular synapse and bypass or bridge areas of neurological damage, thereby causing muscles to contract or relax as needed. More specifically, in the preferred embodiment of the invention, the electric current is applied to an area right above an area of neurological damage, where it bypasses or bridges the area of neurological damage, and travels to an area below the damage in order to stimulate muscle. This process requires an understanding of where a neurological signal was coming from above the area of neurological damage as well as where that signal needs to travel to, such as directly in the spinal cord or in a muscle or muscle group itself, in order to correctly stimulate muscle. This is an important process in the present invention. One of the main reasons that people with neurological damage cannot function as normal and move their limbs is because the muscles required for movement cannot receive signals from neurons to stimulate the muscles. There is generally an area along the synaptic pathway that is damaged such that a signal generated in the brain to move the muscle cannot reach its intended target muscle due to this damage. By creating a bypass, electric current as applied in the present invention can reach the intended target muscle, allowing an individual to move that muscle as normal. Thus the present invention can precisely target motor nerve roots, and also peripheral neurons that are responsible for general or specific areas of the body and that can be injured such that their function is compromised, essentially reversing the effects of neurological damage.

Not only can the electric current can be applied above an area of neurological damage and bypass or bridge damaged nerve areas as stated above, but also below an area of neurological damage directly without the need for a bypass or bridge. Therefore, the present invention provides for a method of stimulating muscle in a person having neurological damage by applying electric current to nerves, thereby moving the muscle in a natural manner. This method is especially useful when a very specific muscle group is desired to be moved or a person only desires to have their muscle perform a specific function. In this case, it is not necessary to bypass or bridge an area of neurological damage. For example, this method can be useful in providing bowel or urinary tract function control in individuals who have lost such control such as by providing sphincter function to contract or relax muscles or tone via S2-S4 stimulation or stimulating nerves related to urinary tract control with detrusor function to cause the urinary tract muscles to contract or relax to control urine flow, or providing sexual function when loss has occurred by stimulating nerves related to sexual function. This method can also be useful for exercise or stimulation of muscles of individuals, in rehabilitation of particular muscles, or in space where astronauts can suffer from loss of muscle tone due to low gravity. The method of stimulation for exercise is further described below.

The methods of the present invention, along with the appropriate contacting electrodes 12, and computer algorithm(s) of the motor device 10, are useful to allow person control, and are intended to allow persons to move digits, limbs and other body parts that have become paralyzed due to trauma and/or disease resulting from a broad spectrum of causes and especially by loss of nerve function. Thus, in the successful use of this invention, a paralyzed individual can become capable of standing, flexing muscles, and motility such as walking. In other words, use of the device 10 of the present invention can allow an otherwise paralyzed person to regain function of their body. This invention can be used as an interventional treatment for persons who are paralyzed due to spinal cord involvement. This invention can be used as an interventional treatment for persons having arm paresis due to a cerebrovascular accident or stroke. This invention can also be used to treat persons who, due to spinal cord injury, have lost feeling in specific parts of the body. Additionally, this invention can be used to reduce or eliminate the feeling of pain felt at peripheral locations by those individuals who feel chronic pain. The methods and device 10 disclosed herein can be used with any individual that has neurological damage.

The present invention provides more specifically for a method of moving muscles of a paraplegic, by applying electric current to nerves, bypassing or bridging an area of neurological damage, and moving normally non-functioning muscles, and thereby moving normally non-functioning limbs. By using the motor device 10 as explained above, this method can allow a paraplegic to regain function of any part of the body that had been rendered non-functioning by their condition. For example, by applying electric current to appropriate nerves, muscles required for walking can be stimulated and moved, thereby allowing the individual to walk by moving their legs.

The present invention further provides for a method of reducing or eliminating pain from an individual, by applying electric current to nerves, bypassing or bridging an area of neurological damage, and reducing or eliminating pain. Preferably, this method is performed by using the device 10 described above. The electric current acts to influence the processing of information within the central nervous system, and increase peripheral blood flow. The intrinsic nervous system of a muscle is interposed between the information processing of the central nervous system and muscle function, so the electric current can modulate the processing of the pain experienced at the muscle. The device 10 can be placed following the nerve root in order to reduce and eliminate pain The present invention further provides for a method of treating foot drop, by applying electric current to nerves, bypassing or bridging an area of neurological damage, and regaining feeling and function of a damaged foot. In foot drop, the individual is unable to lift, or finds difficulty in lifting, the front of the foot when walking. This method is preferably performed by using the device 10 as described above.

This condition can result from direct injury to the spinal cord, along with degenerative conditions such as multiple sclerosis. A recent treatment for this condition uses the Ness L300 system (Bioness, Inc, Valencia, Calif.). This system provides electrical stimulation to peripheral muscles, specifically the anterior tibialis, in response to the foot being lifted from the ground. No other nerves involved in walking are influenced by the Ness L300. The present invention provides a distinct improvement on the Ness L300. In the resulting improvement, the electrical stimulation is directed at the nerve root in the spinal cord, for example, at neurologic level L4, thereby allowing the individual to both flex the foot and lift the leg while walking, which more closely resembles the gait of a healthy individual. Along with allowing greatly improved motility, the use of the present invention can reverse or dramatically diminish the extent muscle atrophy.

The method of the present invention can be used as a combination treatment with other therapies that are currently used for treating neurological damage, or whose use is currently under investigation. For example, the present invention provides for a method of stimulating muscle in a person having neurological damage by treating the person with stem cells, applying electric current to nerves, bypassing or bridging an area of neurological damage, and moving the muscle in a natural manner. This method is especially helpful when the current therapy can be expected take months or years to take effect, if at all. Stem cell therapy applied to the spinal column may not produce results for five years or more. In the meantime, by combining the stem cell treatment with the present invention, muscle can be stimulated, exercised, and strengthened in anticipation of the treatment being effective. Thus, the electrical stimulation can have an adjuvant effect with stem cell treatment in providing the restoration of natural function. This method is preferably performed by using the device 10 as described above.

The method of the present invention can also be used as a therapeutic method for exercising for an individual with neurological damage by applying electric current to nerves, bypassing an area of neurological damage, and stimulating and exercising muscles that otherwise would not be stimulated due to the neurological damage. This method allows an individual's muscles to be exercised through contraction and relaxation and to grow stronger over time due to the stimulation by electric current. This method of exercise is more natural than by exercising with machines or a physical therapist, as the there is less risk of damage to muscles due to natural movement through the electrical stimulation. While an individual may not be strong enough at first to use certain muscles, over time by performing this method, the individual can build stronger muscles and eventually use the limbs that the muscles control. This method is preferably performed by using the device 10 as described above. The method can also include the steps of increasing muscle bulk and strength, independent of function. This can allow for core muscle groups, such as abdominals and paraspnals to be bulked up, helping with stability and preventing deformity.

With all of the methods of the present invention, therapy and rehabilitation with a therapist can be required to train a person to become comfortable with the capabilities of the device as well as the restrictions of their own body. Initially, the movements can be difficult to control, and working with a therapist allows for the right parameters to be programmed into the device 10 to provide natural movement. This also allows the person to get used to the flow of current and the meaning of the current in terms of movement of the body.

The device 10 and methods of the present invention can also be used in combination with a mobile standing device, such as, but not limited to, the STANDING DANI® (Davis Made, Inc.) as well as other such assistive devices. Once the device 10 is implanted in the person, the mobile standing device can be a failsafe where the person can gradually become further and further in control of their own legs as they become comfortable with the programming and become stronger. The device 10 can be used in like fashion in combination with other such assistive devices, another example of which includes devices for upper limb rehabilitation used to regain arm function following stroke. Thus, device 10 can broadly be applied in cases of paralysis or other movement-related disorders of the body.

The device 10 of the present invention overcomes the problems of electrical stimulation devices of the prior art because multiple muscles or areas of muscles can be stimulated at once, thereby allowing for natural movement of muscles and elimination of damage of muscles due to contraction without corresponding relaxation. An indirect positive outcome is that causing muscular contraction can stimulate bone regeneration, thereby making bones stronger, or at least reducing the rate of bone loss. The use of motor nerve roots is a more elegant solution than is the use of peripheral transcutaneous stimulation or transepithelial stimulation (TES): it is applied at the spinal cord at the level of injury, can eliminate the muscle tears, blisters, rashes, burns, and dizziness found with percutaneous TES. This method can overcome a major disadvantage of poor stimulation selectivity and allow more natural walking patterns than surface electrodes, thus being more suited as a prosthetic device for chronic use. The present invention also improves on commercially available pulse generators because of the multiplicity of electrodes 12 per nerve root. Nerve root stimulation also can interact with the central pattern generator of locomotion, which represents organization among spinal neurons. Activating the central pattern generator can cause coordinated muscle contraction as in locomotion, and so can result from stimulation of a small number of sites on the nerve roots. The present invention provides the capability of fine-tuning such stimulation.

The motor device 10 can also be electronically connected to a sensory device 40, shown in FIG. 2 (not shown to scale), having a biofeedback mechanism 42 to send information to the spinal cord and sensory nerves and the brain as a part of a biofeedback loop so that the person can "sense" the movement. Information harvested from the motor stimulation can be sent to a spot above the level of spinal cord injury to an intact segment to then help the body "feel" the movement. The information can be sent by wired communication or wireless communication between the motor device 10 and the sensory device 40. The sensory device 40 can further include computer storage and algorithm mechanisms to control and send information stored on non-transitory computer readable medium. Both the motor device 10 and the sensory device 40 can be independently programmable via an external source. Therefore, the present invention provides for a biofeedback system including the motor device 10 in electronic communication with the sensory device 40 having the biofeedback mechanism 42 to send information generated by the motor device 10 to the spinal cord. The sensory device 40 can include electrodes 12, which can have any of the properties or construction as described above. The sensory device 40 can be any suitable sensor known in the art that can sense various biological properties of an individual.

The present invention further provides for a method of generating movement of muscle and sensing that movement in a person having neurological damage, by applying electric current to nerves, bypassing an area of neurological damage, moving the muscle in a natural manner, and sending information of the movement to the spinal cord, thereby allowing the person to sense the movement. Preferably, this method is performed by using the motor device 10 and sensory device 40 as described above. Each of these steps has been described above, with the applying, bypassing, and moving steps being performed by the motor device 10, and the sending (and sensing) step being performed by the sensing device 40. This method allows an individual with neurological damage and inability to move muscles in a normal manner to move those muscles as well as sense that movement.

In one example of this method, if a person has a T10 paraplegia, the device 10 can be hooked up such that it now bridges the T10 injury at approximately the T8 or T7 level and as the device 10 is turned on, unique sensory signals can be sent back to the brain via the intact spinal cord at around the T7 level, thereby creating a biofeedback loop and the person is then aware of the motion of their legs through true sensory patterns which are unique for every particular motion.

Also, the biofeedback loop can be completed by linking the motor device 10 to an information harvesting device 50 that includes a mechanism 52 for harvesting information directly from the brain and motor cortex, as shown in FIG. 3. The information harvesting device 50 can then send information to the motor device 10 to create a complete parallel structure referred to as an "artificial spinal cord". Again, the information can be sent by wired communication or wireless communication between the information harvesting device 50 and the motor device 10. This allows the person to directly control the movement of muscles that are stimulated by the motor device 10 instead of relying on a program to activate the electrical stimulation of the muscles. The information harvesting device 50 can further include any computer or algorithm mechanisms as necessary to communicate with the motor device 10, stored on non-transitory computer readable medium. Essentially, the information transmitted by the information harvesting device 50 is translated by the motor device into electric current needed to apply to the nerves. The information harvesting device 50 can be a sensor known in the art that is capable of sensing signals from the brain and motor cortex.

Therefore, the present invention provides for an artificial spinal cord including the motor device 10 as described above for bypassing an area of neurological damage in communication with the sensory device 40 having the biofeedback mechanism 42 to send information generated by the motor device 10 to the spinal cord, and the motor device 10 being in communication with the information harvesting device 50 having the mechanism 52 to harvest information directly from the brain and motor cortex and send to the motor device 10.

The present invention further provides for a method of generating movement of muscle and sensing that movement in a person having neurological damage, by harvesting information directly from the brain and motor cortex to move muscle, translating the information into the application of electric current to nerves, bypassing an area of neurological damage, moving the muscle in a natural manner, and sending information of the movement to the spinal cord, thereby allowing the person to sense the movement. Each of these steps is described above and these are preferably performed by the motor device 10, the sensory device 40, and the information harvesting device 50, and by performing this method, a person having neurological damage can bypass their own spinal cord and areas of neurological damage. The person can generate the signal to move their own muscles, allowing them to move in a natural manner. This method is especially useful to those people who have significant damage to their own spinal cord.

The motor device 10 of the present invention can further be used in a diagnostic method by applying electric current to nerves, measuring movement of muscle due to the electric current, and based on the amount of muscle movement, diagnosing a person as having neurological damage. This method can be used to determine whether there has been neurological damage to an area of the body, as well as to determine whether a certain amount of electric current can bypass the area of neurological damage to stimulate and move the muscle. If a muscle fails to move or moves less than expected, then neurological damage has occurred. This method can be used to determine how effective the electric current is at bypassing the area of neurological damage and moving the muscle. The steps of this method are essentially performed as describe above. The electric current can be applied to any nerves in the body in this method.

Any of the above methods can be combined to produce different results in the body. For example, the method of reducing or eliminating pain can be combined with the method of stimulating muscle in a person having neurological damage, as shown in Example 3. In other words, the device 10 can provide several different positive effects in the body, depending on the particular needs of the person.

The present invention provides many advantages over the prior art. The present invention utilizes circumferential electrode bodies that maintain direct contact around the circumference of the nerve root. A multiplicity of electrical contacts are placed within the electrode body and thereby are placed in immediate proximity to the nerve. These multiple contacts are placed in direct contact with the nerve surface, so to allow a fine degree of control over the location, intensity, phase and other characteristics of each of the electrical fields that are applied to the nerve root. This is of particular significance when stimulating a nerve root, due to the presence of multiple nerve fascicles within the nerve root. Thus, the present method allows a very fine degree of control in stimulating nerves within the nerve roots, which by its design improves on prior art methods described above. Direct circumferential contact of nerves, by the device in the present invention, thus has advantages that include a finer and more targeted current applied directly to the surface of the nerve; reduced current demands that lower the potential for tissue damage and minimize energy consumption; and more consistent contact of all electrical contacts within the electrode body.

The invention is further described in detail by reference to the following experimental examples. These examples are provided for the purpose of illustration only, and are not intended to be limiting unless otherwise specified. Thus, the present invention should in no way be construed as being limited to the following examples, but rather, be construed to encompass any and all variations which become evident as a result of the teaching provided herein.

EXAMPLE 1

Under the supervision of the onsite veterinarian, and under aseptic conditions, rats were anesthetized and kept under conscious sedation with appropriate analgesics, as per the veterinarian. Local anesthetics were injected and a midline incision was made getting down to the lamina. Laminontomies and laminectomies were performed utilizing a high speed Midas Rex Drill. The dura and nerve roots were exposed and epidural leads were directly placed over the top of the nerves. Electrodes were subsequently connected to the neuromodulator device, which when activated caused motor contractions in the corresponding muscles. Quantitative results could not be obtained due to the large size of the electrodes relative to the very small fine nerves of the rat, which caused difficulty in reproducible electrode placement. However, the observation was made in every case that spinal cord nerve root stimulation caused motor contractions in the corresponding muscles.

EXAMPLE 2

In the course of electrode placement for treatment of pain in a paralyzed person, an eight-contact epidural lead was placed at the foramen covering the nerve roots at neurological levels L5 and S1. This procedure was performed by a neurosurgeon using a cannulated catheter and was guided by fluoroscopy. The act of programming of the spinal cord stimulator caused the person's foot to flex. This result indicates that motor nerve root stimulation in the spinal cord can, indeed, cause contraction of corresponding muscles.

EXAMPLE 3

John is a 47 year old male who underwent multiple spine surgeries and ended up having chronic back pain as well as left leg pain and weakness requiring neuromodulation. Multiple medications were tried and ultimately, he required a spinal cord stimulator to be placed in his thoracic level to try to control his pain. This helped him with is back pain but did not fully control his leg pain and the pain that was distributed down his L5-S1 nerve root level was persistent despite the neuromodulator taking away part of his pain. In these difficult cases, retrograde leads can be utilized following the nerve root and this can take away the pain. The patient had an eight electrode linear array placed along the nerve root at the L5-S1 level, parallel to the S1 nerve root. This produced paresthesia thereby decreasing the patient's pain. It was placed in a manner that it also was capable of causing motor stimulation, therefore this was exploited in a post operative period to cause his leg to move.

The procedure was done through a laminotomy approach with a paramedian incision in the back over approximately the L5-S1 level. A drill hole was placed into the lamina and then got into the epidural space where the lead was placed in. The leads were secured to the soft tissue with a lead anchor and tunneled in a subcutaneous fashion to a Boston Scientific generator.

Once the procedure was done and the device was being held in place, appropriate foot and leg movement was programmed and caused. This was done a few days later and thereby proves the concept of foot motion utilizing neuromodulation within the realm of the currents and voltages generated.

Figure 6:
FIG. 6 is a photograph of an electrode at the nerve root.
Figure 7:
FIG. 7 is a photograph of an electrode at the nerve root.

The area that was stimulated was mainly the S1 nerve root and one could see muscle contractions with his leg movement as a result of stimulation. As shown in FIGS. 6 and 7, the electrode hugs the nerve root.

EXAMPLE 4

In this case study multiple electrodes were placed from L2 to S1 along the nerve roots of a T5 traumatic paraplegic patient who had not moved her legs for two years. By connecting to battery power and using computer algorithms to modulate individual nerve roots, precise and synchronous myotome movements were achieved.

Methods

The patient is a 32 year old female left with complete T5 paralysis for two years after suffering a T5 burst fracture after falling from a tree. She had cord compression in the cervical spine causing full return of upper extremity function. T5 posterior fusion and decompression was performed to stabilize her but the injury was complete, with no return of function after two years. A baclofen pump was inserted into the L3 level for spasticity months later. She remained a highly motivated, positive patient despite the devastating injury.

After obtaining informed consent from the patient, a total of 8 leads with 8 electrodes each were implanted at L2, L3, L4, and S1 bilaterally. 4 leads for a total of 16 electrodes on each nerve root with two leads each were implanted at L5 bilaterally.

The procedure was performed under general anaesthetic with a small laminotomy at T12 to facilitate retrograde insertion of percutaneous leads to each level. The anatomy of the interlaminar space would not allow for an appropriate trajectory of insertion without a laminotomy. A laminotomy may be avoided by using extra foraminal approaches to each nerve root, antegrade placement with significant bends on introducers wires or in patients with large interlaminar space anatomy or direct surgical cut downs to each level. The current approach was taken to minimize surgical time and achieve the highest accuracy of placement. Total surgical time was approximately 120 minutes.

A total of 2 batteries with four ports each were utilized connecting 8 electrodes to D port for S1, 16 electrodes with a splitter to C port, 8 electrodes from L4, and 8 electrodes to L3 with a splitter to B port and 8 electrodes to A port form L2.

Figure 9:
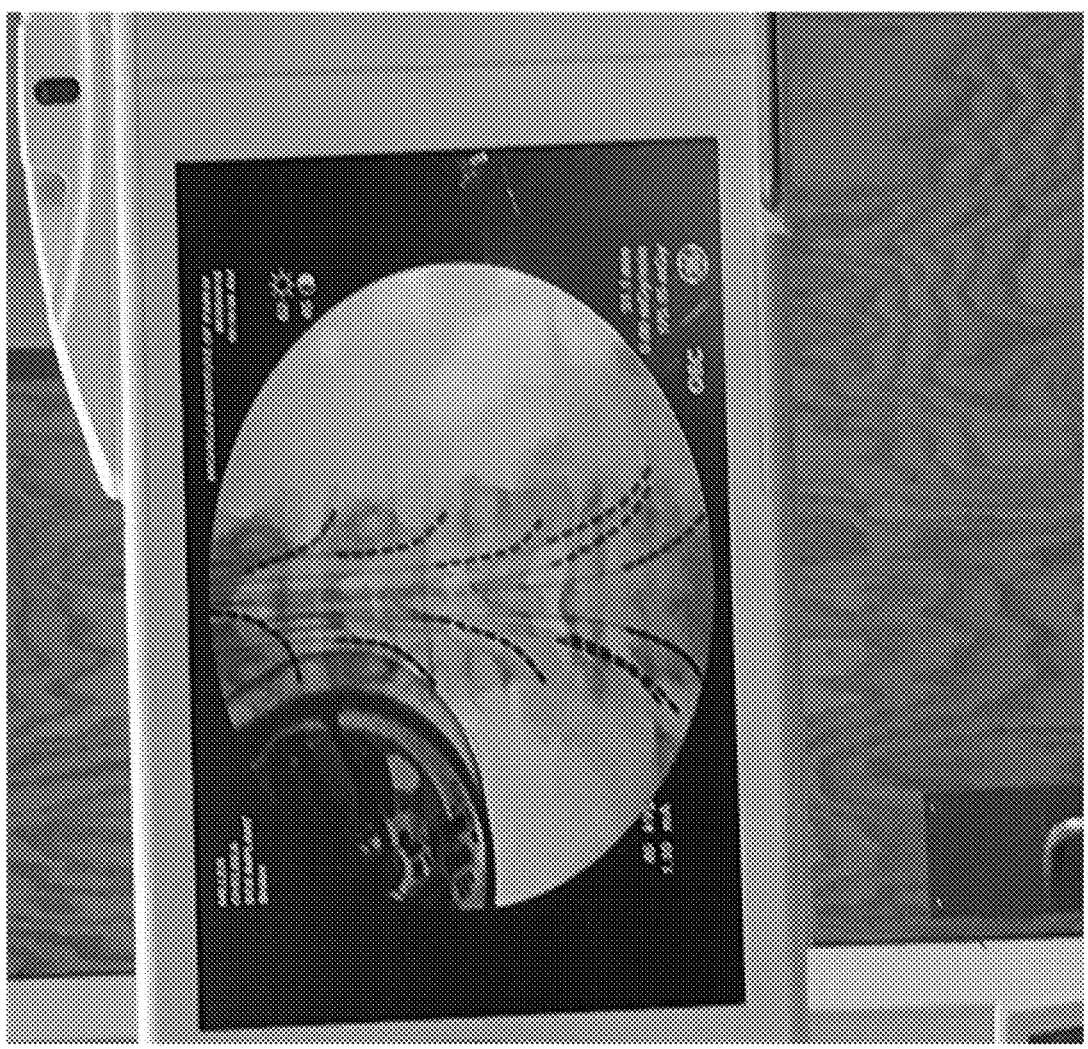
FIG. 9 is a photograph of placement of the motor device in a patient.

They were anchored into the interspinous ligament and tunneled to two separate gluteal pockets on either side. All electrodes from the left were sent to the left battery and right electrodes to the right battery. This allowed for a total of 64 contact points (32 per battery) on 12 leads with implantation of 96 electrodes that covered L2 to S1 bilaterally. A larger array of leads and batteries can be used for similar patients as resources become more readily available. Each lead hugged the posterolateral gutter of the spinal canal before exiting along with the nerve root out the respective foramen (see FIG. 9).

After recovery, the patient was sent home the same day and allowing one week for healing, the patient was brought to an outpatient setting and programming ensued.

Motor movement was evaluated with the following:
0 no movement
1 trace licker
2 very weak cannot lift against gravity
3 can resist gravity
4− weak but stronger then 3
4 moderate strength less then normal
4+ moderate strength less then normal
5 normal strength
Observations are shown in TABLE 5.

TABLE 5

| L2 | Right | knee extension 4+ |
| | | hip abduction 4− |
| | | ankle and toe extension 3 |
| | Left | knee extension 4+ |
| | | hip abduction 4− |
| | | ankle and toe extension 3 |
| L3 | Right | 3 |
| | Left | 3 |
| L4 | Right | 3 |
| | Left | 3 |
| L5 | Right | 3 |
| | Left | 3 |
| S1 | Right | 3 |
| | Left | 3 |

Function was evaluated of standing, leg bending at knee, leg extension at knee, leg strengthening currently measuring calf and thigh circumference, and straightening.

Problems reported were goosebumps, no blood pressure or heart rate changes (could happen if stimulation is perceived as irritating or painful to the nerve root, different parts of the nerve root and different configuration produce different results, and possible nerve root or muscle damage by prolonged stimulation and fatigue or too high a voltage or intensity.

CONCLUSION

This case report demonstrates the ability to modulate motor nerve roots in precise, replicable and targeted manners. This will certainly help in increasing muscle mass, and has proven function can also be achieved. This indicates that the next era for motor neuromodulation of the nerve roots brings promise to reanimation of paralyzed limbs. The current patient has shown a variety of increasing abilities to weight bare and move her legs in a controlled fashion with improvement being achieved on a weekly basis. A cuff lead with circumferential electrodes with the smallest possible contact points will allow greater variety of electron clouds to be delivered leading to more diverse functional effects.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

What is claimed is:

1. A motor device for stimulating muscle, comprising:
at least one electrode for generating electric current operatively attached to an electrode array and exposed on an inner surface of an array body, wherein said electrode array is in a shape of a cuff configured for wrapping around a nerve root, and a programming mechanism of a computer that executes an algorithm stored on a non-transitory computer readable medium and includes an information storage mechanism and a user-operated interface in electrical connection with said at least one electrode for programming operation of said at least one electrode, said motor device being configured to be implanted in an individual and being configured to apply electric current to the nerve root at an area above an area of neurological damage, wherein said algorithm is configured to set each of parameters of timing of electrical potential applied at different electrodes in said electrode array, varying the intensity of electrical current applied at different electrodes in said electrode array, use of variable frequency trains, relaxation kinetics, stimulation frequency, shortening history, constant stimulation, randomized frequency, randomized current amplitude, and randomized pulse width, and wherein said algorithm is configured to provide coordinated muscle stimulation and provide fluid movement.

2. The motor device of claim 1, wherein each said at least one electrode further includes a wire lead that passes through said array body and exits at an outer surface and is connected to a source of electric current.

3. The motor device of claim 2, wherein said wire lead is coated with an insulating polymer chosen from a group consisting of silicones, photo-patternable silicone, hydroxylated urethane, polyimides, polytetrafluoroethylene, and flexible polymers having a high dielectric constant.

4. The motor device of claim 2, wherein said at least one electrode is made of a material chosen from a group consisting of surgical stainless steel, gold wire, indium/gold alloy, photo-patterned gold, and layers of photo-patterned chromium and gold.

5. The motor device of claim 1, wherein said array body has a long axis of 2 to 3 cm.

6. The motor device of claim 1, wherein said array body has a short axis of 2.3 to 2.8 cm.

7. The motor device of claim 1, wherein multiple electrodes are arranged in circumferential rows along said inner face.

8. The motor device of claim 7, wherein said multiple electrodes are arranged in lines of dots 0.1 to 2.5 mm in diameter.

9. The motor device of claim 8, wherein said lines are 1 mm to 1 cm apart.

10. The motor device of claim 1, wherein said array body is made of a material chosen from a group consisting of silicones, photo-patternable silicone, hydroxylated urethane, polyimides, polytetrafluoroethylene, polyurethane, and polydimethylsiloxane.

11. The motor device of claim 1, wherein said electrode array further includes multiple flaps having holes for suturing within an individual's body.

12. The motor device of claim 2, further including a battery in electrical connection with said wire lead.

13. The motor device of claim 1, wherein said computer is in electronic communication with a remote interface chosen from a group consisting of a smart phone, a touch screen device, a voice-activated device, and a thought-activated device.

14. The motor device of claim 1, further in electronic communication with a sensory device including a biofeedback mechanism for sending information generated by said motor device to the spinal cord.

15. The motor device of claim 14, wherein said sensory device is programmable and includes computer storage and an algorithm stored on non-transitory computer readable medium for controlling and sending information.

16. The motor device of claim 14, further in communication with an information harvesting device including a mechanism for harvesting information directly from the brain and motor cortex and sending said information to said motor device, wherein said motor device, sensory device, and information harvesting device act as an artificial spinal cord.

* * * * *